United States Patent
Cabiri

(10) Patent No.: US 11,141,566 B2
(45) Date of Patent: Oct. 12, 2021

(54) STEERING TOOL

(71) Applicant: Bendit Technologies Ltd., Petach Tikva (IL)

(72) Inventor: Oz Cabiri, Hod HaSharon (IL)

(73) Assignee: Bendit Technologies Ltd., Petach Tikva (IL)

( * ) Notice: Subject to any disclaimer, the term of this patent is extended or adjusted under 35 U.S.C. 154(b) by 182 days.

(21) Appl. No.: 15/344,524

(22) Filed: Nov. 6, 2016

(65) Prior Publication Data

US 2018/0126122 A1 May 10, 2018

(51) Int. Cl.
| | |
|---|---|
| *A61M 25/01* | (2006.01) |
| *A61B 1/005* | (2006.01) |
| *A61B 17/12* | (2006.01) |
| *A61M 25/00* | (2006.01) |

(52) U.S. Cl.
CPC ....... *A61M 25/0113* (2013.01); *A61B 1/0055* (2013.01); *A61B 1/0057* (2013.01); *A61B 17/1214* (2013.01); *A61M 25/0043* (2013.01); *A61M 25/0138* (2013.01); *A61B 2017/1205* (2013.01); *A61M 25/0147* (2013.01); *A61M 2025/0175* (2013.01)

(58) Field of Classification Search
CPC . A61B 1/0055; A61B 1/0057; A61B 17/1214; A61M 25/0043; A61M 25/0138
USPC ...................................................... 600/585
See application file for complete search history.

(56) References Cited

U.S. PATENT DOCUMENTS

| | | | |
|---|---|---|---|
| 3,802,440 A | | 4/1974 | Salem |
| 9,782,566 B1 * | | 10/2017 | Paprocki ........... A61M 25/0041 |
| 2014/0187983 A1 * | | 7/2014 | Anderson ............ A61B 5/6851 |
| | | | 600/486 |
| 2015/0099997 A1 * | | 4/2015 | Cabiri .............. A61B 17/00234 |
| | | | 600/585 |
| 2016/0310702 A1 * | | 10/2016 | Cabiri ............... A61M 25/0136 |
| 2018/0008805 A1 * | | 1/2018 | Pleijers ................ A61B 1/0011 |

FOREIGN PATENT DOCUMENTS

| | | |
|---|---|---|
| WO | 2006/012668 | 2/2006 |
| WO | 2015/095475 | 6/2015 |
| WO | 2016/160694 | 10/2016 |

OTHER PUBLICATIONS

PCT Search and Written Opinion PCT/IB2017/056913, dated May 2, 2018.

* cited by examiner

*Primary Examiner* — Daniel L Cerioni
(74) *Attorney, Agent, or Firm* — Dekel Patent Ltd.; David Klein

(57) ABSTRACT

A steering tool includes an internal tube disposed inside an external tube. The internal and external tubes are arranged for longitudinal axial movement relative to one another. A distal portion of the internal tube is fixedly joined to a distal portion of the external tube. At least one of the tubes may include, over at least some of its length, two continuous, longitudinal zones of solid material separated from each other by a longitudinal gap. At least one of the tubes may include a flexible distal portion distal to the joining zone, the flexible distal portion being more flexible than other portions of that tube.

9 Claims, 2 Drawing Sheets

STEERING TOOL

FIELD OF THE INVENTION

The present invention generally relates to a steering tool for steering medical devices through body lumens.

BACKGROUND OF THE INVENTION

PCT Patent Application PCT/US2013/040691, to the present inventor, describes a steering tool for steering medical devices through body lumens. The steering tool has an internal tube disposed inside an external tube. The internal and external tubes are arranged for longitudinal axial movement relative to one another. The distal end of the internal tube is fixedly joined to the distal end of the external tube. One or both of the internal and external tubes is slotted near the distal end thereof. The longitudinal axial movement causes bending of the distal ends of the tubes. One or both of the internal and external tubes are slotted near the distal ends thereof. The steering tool provides a distal tip which combines steerability, flexibility and torqueability. The tool eliminates the need for pull/push wires.

Some of the advantages of that steering tool include reduced cross section, circular cross section in each direction for uniform stability of bending in different directions (towards two or more sides), very thin wall thickness, and applicability to very small tubes (e.g., diameters of 0.2-3 mm). The steering tool also works well with larger tubes. The steering tool simplifies production and reduces the number of parts for any steerable tool in medical and industrial fields.

SUMMARY OF THE INVENTION

The present invention seeks to provide further improvements to the steering tool for steering medical devices through body lumens, as is described more in detail hereinbelow.

There is thus provided in accordance with an embodiment of the present invention a steering tool including an internal tube disposed inside an external tube, the internal and external tubes being arranged for longitudinal axial movement relative to one another, wherein a distal portion of the internal tube is fixedly joined to a distal portion of the external tube at a joining zone, and at least one of the internal and external tubes is formed with transverse slots near the distal end thereof, and wherein the longitudinal axial movement causes bending of the distal ends of the tubes, and wherein at least one of the tubes includes, over at least some of its length, two continuous, longitudinal zones of solid material separated from each other by a longitudinal gap.

In accordance with an embodiment of the present invention at least one of the tubes includes a flexible distal portion distal to the joining zone, the flexible distal portion being more flexible than other portions of that tube. The flexible distal portion may be formed with helical grooves.

In accordance with an embodiment of the present invention a covering is provided over the flexible distal portion. The covering may or may not be softer than the flexible distal portion.

In accordance with an embodiment of the present invention the covering includes a transmitter or receiver.

In accordance with an embodiment of the present invention at least one of the tubes includes a most proximal portion, a middle portion and a most distal portion, wherein the most distal portion is more flexible than the middle and the most proximal portions, and the most proximal portion is more axially stiff than the middle and the most distal portions.

In accordance with an embodiment of the present invention the gap includes a separation line plus apertures formed through the gap, axially separated from each other longitudinally along the gap. The apertures may be stadium (rectangle with round ends) shaped, for example.

In accordance with an embodiment of the present invention the internal and external tubes are each formed with one or more alignment holes for correct axial and rotational alignment of the internal and external tubes during joining and assembly.

There is also provided in accordance with an embodiment of the present invention a steering tool including an internal tube disposed inside an external tube, the internal and external tubes being arranged for longitudinal axial movement relative to one another, wherein a distal portion of the internal tube is fixedly joined to a distal portion of the external tube at a joining zone, and at least one of the internal and external tubes is formed with transverse slots near the distal end thereof, and wherein the longitudinal axial movement causes bending of the distal ends of the tubes, and wherein at least one of the tubes includes a flexible distal portion distal to the joining zone, the flexible distal portion being more flexible than other portions of that tube.

In accordance with a method of the present invention, the steering tool may be used to push, pull or guide a camera, an electrical energy device, an illumination device, a thrombectomy device, a fiber optic device or a laser device to a treatment site.

The steering tool has many applications in the delivery of tools or substances through body lumens. One exemplary application is that of endovascular coiling to treat cerebral aneurysms. In the prior art, a coil is delivered to the aneurysm in an effort to promote blood clotting around the coils, so as to seal the aneurysm and/or reduce pressure on the blood vessel wall. In the prior art, the coil is delivered from the distal end of a microcatheter. Many aneurysms require delivering more than one coil in order to achieve high packing density. There are several challenges in delivering more than one coil. For example, in order to engage the aneurysm, it is difficult to correctly aim and position the tip of the coil delivery tool inside the aneurysm. Another example is the difficulty to maintain the tip of the delivery tool stable while injecting the coil into the aneurysm, and at the same time, avoid a kick back effect of the tip. Yet another example is the difficulty to re-position the tip inside the aneurysm to deliver another coil in the remaining open space without retracting the delivery tool. In the prior art, the delivery tool (catheter) must be retracted, then re-entered at a different catheter angle. In contrast to the prior art, in the steering tool of the present invention, the steering tool does not have to be retracted, but rather stays in place and the operator simply rotates the tip to correctly aim the tip, and the tip remains stable.

As another example, in the prior art, it is difficult to guide a catheter from the aortic arch to the common carotid arteries, and from there to the carotid arterial branches to the brain. This can be especially difficult with patients in which the aortic arch is blocked, such as with calcifications, or is weak and deformed, such as in older patients. In contrast, the steering tool of the present invention is steerable through lumens with many bends and maintains a good level of torque and pushability throughout the bends, so that the steering tool can negotiate the required bends from the aortic arch to the common carotid arteries and the carotid arterial branches, even in the presence of calcifications.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1:
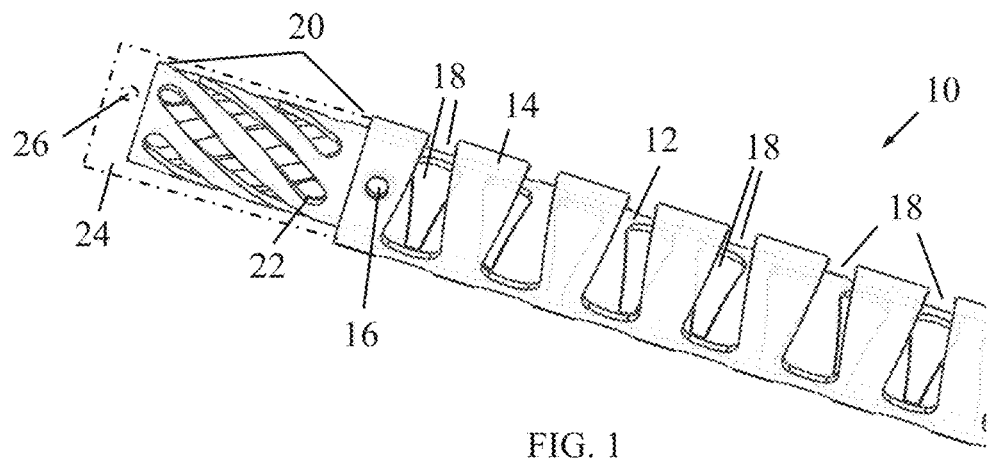
FIG. 1 is a simplified illustration of a distal portion of a steering tool, in accordance with a non-limiting embodiment of the present invention.

Reference is now made to FIG. 1, which illustrates a steering tool 10, in accordance with a non-limiting embodiment of the present invention.

Steering tool 10 includes an internal tube 12 disposed inside an external tube 14. A distal portion of internal tube 12 is fixedly joined to a distal portion of external tube 14 at a joining zone 16 ("joining" is defined below). The joining zone, for any of the embodiments, may be distanced from the distal tip of the tubes or may be at the distal tip of the tubes. The internal and external tubes 12 and 14 are arranged for longitudinal axial movement relative to one another (except for their distal portions which are joined together), which causes bending of the distal ends of the tubes 12 and 14. One or both of the internal and external tubes 12 and 14 may be formed with transverse slots 18 near the distal end thereof. In the illustrated embodiment of FIG. 1, both of the internal and external tubes 12 and 14 is formed with transverse slots 18.

Internal and external tubes 12 and 14 may be made of any suitably flexible, medically safe material, such as but not limited to, stainless steel (e.g., AISI 316), nitinol, cobalt-chromium alloy, nickel-titanium alloy, and others, glass fibers, plastics (e.g., nylon, polypropylene, and many others) or combinations thereof.

The term "joining" encompasses any method for attaching the materials of the tubes together, such as but not limited to, welding, ultrasonic welding, thermal bonding, adhesive bonding, molding, and others. For example, joining zone 16 may be an alignment hole formed in one or both of the tubes for helping to register the tubes in proper angular and axial orientation with each other during the joining process. An alignment pin (not shown) may be inserted in the alignment holes to hold the tubes in the proper alignment during joining. The alignment holes may be off-center and/or of two different diameters to ensure that the tubes are not accidentally aligned incorrectly.

As is now explained, a distal portion of one of the tubes may be flexible and expandable. This may be advantageous in the joining process—the flexible and expandable portion can expand during joining (especially helpful for welding or other types of thermal joining) which can compensate for expansion of the tube material due to heating or compensate for the difference in diameter at the joining point, and thus reduce the need to add material that may clog the working channel.

One or both of the internal and external tubes 12 and 14 (in the illustrated embodiment of FIG. 1, it is the internal tube 12) may include a flexible distal portion 20 distal to the joining zone 16. The flexible distal portion 20 is more flexible than other portions of that tube (in the illustrated embodiment, tube 12).

Figure 2:
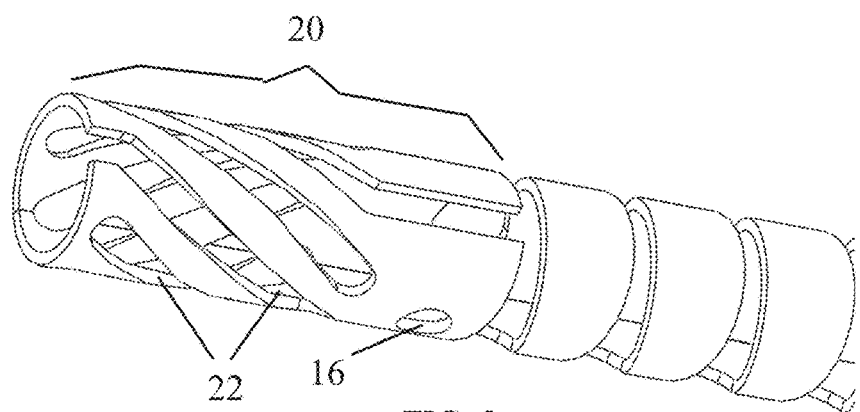
FIG. 2 is a simplified illustration of the steering tool, in accordance with a non-limiting embodiment of the present invention, showing the distal portion of one of the tubes (e.g., the internal tube)
Figure 3:
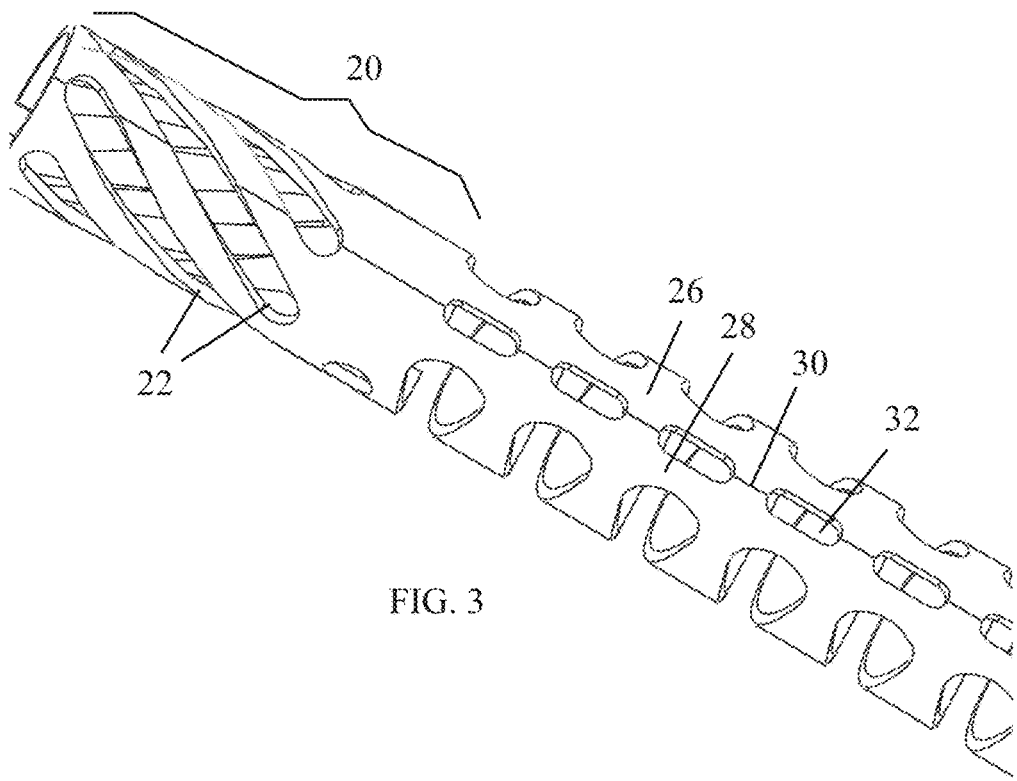
FIG. 3 is another simplified illustration of the distal portion of FIG. 3, showing that the tube includes two continuous, longitudinal zones of solid material separated from each other by a longitudinal gap.

One way of making the distal portion 20 to be flexible is by forming it with helical grooves 22 (seen best in FIGS. 2 and 3). The helical grooves 22 increase the springiness of distal portion 20 and permit distal portion 20 to expand or contract radially during the joining process.

A covering 24 (shown in FIG. 1) may be optionally placed over flexible distal portion 20. Covering 24 may be made of an elastomeric material, such as but not limited to, silicone, rubber, neoprene, latex and others. Covering 24 may be softer than flexible distal portion 20. Covering 24 may include a transmitter or receiver 26, which may be used to transmit positional data of the steering tool tube assembly when negotiating a body lumen. Covering 24 may be kept on the steering tool tube assembly or may be optionally removed before or during use.

Reference is now made to FIG. 3. One or both of the internal and external tubes 12 and 14 (in the illustrated embodiment of FIG. 1, it is the internal tube 12) may include, over at least some of its length, two continuous, longitudinal zones 26 and 28 of solid material separated from each other by a longitudinal gap. The gap may be just apertures 32 spaced axially from each other along a portion of the length of the tube. Alternatively, the gap may include a separation line 30 plus apertures 32 axially separated from each other longitudinally along the separation line 30. The apertures 32 may have a stadium shape (that is, rectangular with round ends). Alternatively, apertures 32 may have other shapes, such as but not limited to, oval, circular, elliptical, polygonal, irregular and others. As another alternative, the gap may be just the separation line 30.

Accordingly, in one aspect of the invention, instead of joining two full tubes (one inner and the other outer) to each other at the ends of the tubes to make the steering device, one of the tubes (preferably, but not necessarily, the inner tube), is not a full 360° perimeter tube, but rather a flexible member formed with a gap. As opposed to the prior art, in which distal ends of two tubes are joined to each other, in this embodiment there is only one tube (the external tube) and there is no inner tube. Instead of the inner tube, a metal strip is bent or rolled or otherwise formed into a curved (e.g., cylindrical) shape, having curved sides separated from each other by a gap (e.g., about 1-1000 microns wide, or more preferably 20-500 microns).

The two continuous, longitudinal zones 26 and 28 of solid material help increase the bending stiffness of the steering tool, yet at the same time, due to the gap, have better resistance to crack or stress failure. The apertures 32 may provide stress relief to increase the resistance to crack or stress failure. This provides risk management, such that in case of a break, the crack does not continue to the second solid line.

Figure 5:
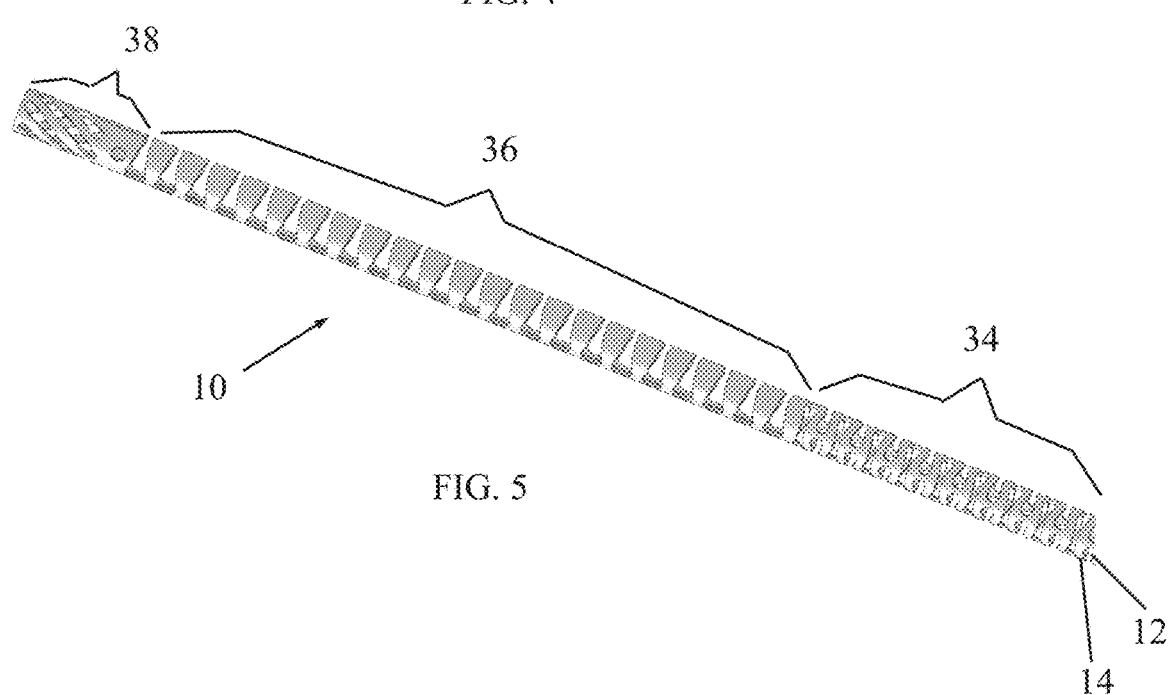
FIG. 5 is a simplified pictorial illustration of the steering tool, showing the most distal portion, middle portion and most proximal portion of the tool.

Reference is now made to FIG. 5. In the steering tool 10, one or both of the tubes 12 and 14 includes a most proximal portion 34, a middle portion 36 and a most distal portion 38. In accordance with a non-limiting embodiment of the present invention, the most distal portion 38 is more flexible than the middle portion 36 and the most proximal portion 34. In accordance with a non-limiting embodiment of the present invention, the most proximal portion 34 is more axially stiff than the middle portion 36 and the most distal portion 38. The two continuous, longitudinal zones of solid material (FIG. 3) may be present in the middle portion 36 and may also be present in the most proximal portion 34. They may also be present in the most distal portion 38.

The middle portion 36 may be flexible for steering through body lumens, whereas the most proximal portion 34 is more axially stiff because it is the portion that connects to a manipulation handle (not shown). The manipulation handle may be as described in PCT Patent Application PCT/US2014/071075 or U.S. patent application Ser. No. 15/057,329.

Figure 4:
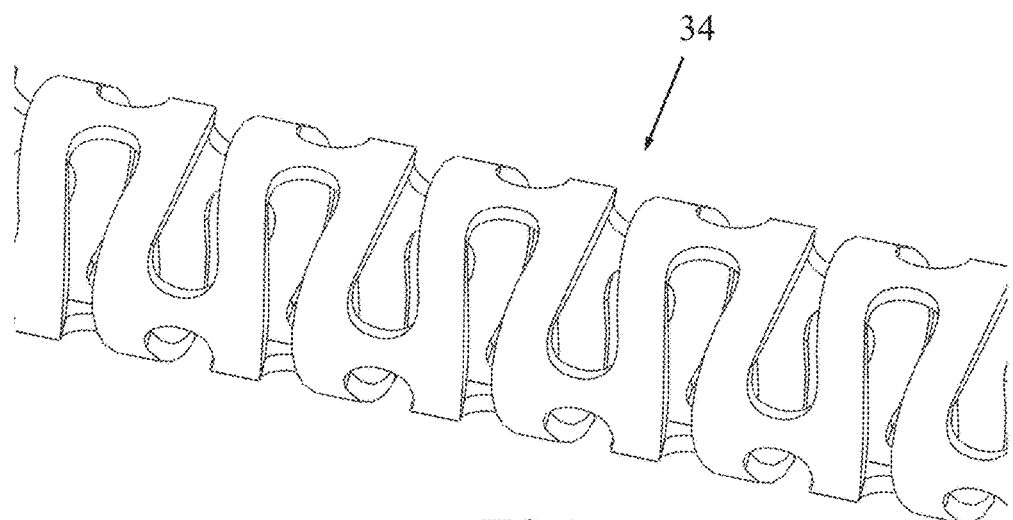
FIG. 4 is a simplified illustration of a proximal portion of the steering tool.

Reference is now made to FIG. 4, which illustrates the proximal portion 34 of the steering tool. The proximal portion 34 may include continuously connected links, which alternate in shape between U-shapes and inverted (upside down) U-shapes. The sides of the U-shapes and inverted U-shapes are not straight, but instead are laterally tilted inwards or outwards. This shape provides good axial rigidity for bearing high axial loads and spreads the load over a plurality of the links, thereby reducing the chance of breaking. The shape is designed not to generate torque (which could happen with spring or diagonal shapes) that would affect the bending mode.

The steering tool can be used to deliver fluids to places in a body with high accuracy, such as but not limited to, direct injection of drugs into the brain. For example, the tool may be used as a needle to protrude through or into a blood vessel and inject substances directly into the brain, tumor or infected area. The steering tool may be used as a catheter to direct and deliver cooled gas to freeze tumors or other areas. The steering tool may be used as a catheter to guide fiber optic or laser devices for illumination, treatment, ablation or drying or other uses.

In any of the embodiments, the distal edge shape of the internal member/tube, external tube and/or overall tool may be not only circular, but also shaped as an electrode, needle or other shapes.

In any of the embodiments, either one or both of the internal member/tube and the external tube may have a portion proximal to the joining zone which is pre-shaped and made of a shape memory material (e.g., nitinol) (such as, without limitation, portion 36 of FIG. 5). The combination of the steerable tip and the pre-shaped, shape memory portion may add further possibilities of the steering tool negotiating differently shaped body lumens. The pre-shaped, shape memory portion may be initially in a somewhat straight or contracted configuration inside a guiding or introducer catheter before deployment out of the catheter, and then revert to its pre-shaped configuration after deployment out of the catheter. Similarly, the pre-shape can be achieved by locally heat-treating the tool at the portion which it is desired to have the pre-shape.

What is claimed is:

1. A steering tool comprising:
    an internal tube disposed inside an external tube, said internal and external tubes being arranged for longitudinal axial movement relative to one another, wherein a distal portion of said internal tube is fixedly joined to a distal portion of said external tube at a joining zone, and said internal tube is not fixedly joined to said external tube at any point distal to said joining zone, and at least one of said internal and external tubes is formed with transverse slots near a distal end thereof, and wherein the longitudinal axial movement causes bending of the distal ends of said tubes;
    wherein at least one of said tubes comprises, over at least some length of said at least one of said tubes, two continuous, longitudinal zones of solid material separated from each other by a longitudinal gap; and
    wherein at least one of said tubes comprises a flexible distal portion which is entirely distal to said joining zone, and wherein said longitudinal gap comprises a separation line that extends into said flexible distal portion.

2. The steering tool according to claim 1, wherein said flexible distal portion is more flexible than other portions of that tube.

3. The steering tool according to claim 1, wherein said flexible distal portion is formed with helical grooves and said separation line extends into one of said helical grooves.

4. The steering tool according to claim 1, further comprising a covering over said flexible distal portion.

5. The steering tool according to claim 4, wherein said covering comprises a transmitter or receiver.

6. The steering tool according to claim 1, wherein at least one of said tubes comprises a most proximal portion, a middle portion and a most distal portion, wherein the most distal portion is more flexible than the middle and the most proximal portions, and the most proximal portion is more axially stiff than the middle and the most distal portions.

7. The steering tool according to claim 1, wherein said gap comprises apertures axially separated from each other longitudinally along said separation line.

8. The steering tool according to claim 3, wherein said helical grooves extend to proximal and distal end faces of said flexible distal portion such that each of the proximal and distal end faces of said flexible distal portion has a circumferential opening.

9. The steering tool according to claim 1, wherein said internal and external tubes are each formed with one or more alignment holes for correct axial and rotational alignment of said internal and external tubes during joining and assembly.

* * * * *